US012708452B2

(12) United States Patent
Fouts et al.

(10) Patent No.: US 12,708,452 B2
(45) Date of Patent: Aug. 18, 2026

(54) SURGICAL TOOL INCLUDING A BLACK POLYMER DISTAL PORTION HAVING TRANSVERSE PLANAR SURFACES WITH LASER-MARKED FIDUCIAL MARKERS

(71) Applicant: Stryker Corporation, Kalamazoo, MI (US)

(72) Inventors: Brian Fouts, Morgan Hill, CA (US); Matthew Urban, Highlands Ranch, CO (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/661,466

(22) Filed: May 10, 2024

(65) Prior Publication Data

US 2024/0374318 A1 Nov. 14, 2024

Related U.S. Application Data

(60) Provisional application No. 63/502,026, filed on May 12, 2023.

(51) Int. Cl.

| | |
|---|---|
| ***A61B 34/20*** | (2016.01) |
| ***A61B 1/313*** | (2006.01) |
| ***A61B 90/00*** | (2016.01) |
| ***A61B 90/92*** | (2016.01) |

(52) U.S. Cl.

CPC .............. *A61B 34/20* (2016.02); *A61B 90/92* (2016.02); *A61B 1/313* (2013.01); *A61B 2034/2055* (2016.02); *A61B 2034/2068* (2016.02); *A61B 2090/3937* (2016.02)

(58) Field of Classification Search

CPC ......... A61B 34/20; A61B 90/92; A61B 1/313; A61B 2034/2055; A61B 2034/2068; A61B 2090/3937; A61B 1/000094; A61B 1/018

See application file for complete search history.

(56) References Cited

U.S. PATENT DOCUMENTS

2010/0168562 A1* 7/2010 Zhao ...................... A61B 34/30 600/426
2015/0173644 A1* 6/2015 Ren ..................... A61F 9/00736 600/424
2015/0297177 A1* 10/2015 Boctor ................... A61B 34/30 901/47

(Continued)

FOREIGN PATENT DOCUMENTS

CN 101267776 A * 9/2008 ............. A61B 90/36
WO WO-2021185811 A1 * 9/2021 ............. A61B 90/39

OTHER PUBLICATIONS

McKee, Terry. "Laser marking." Handbook of Laser Technology and Applications. CRC Press, 2021. 35-45. (Year: 2021).*

(Continued)

*Primary Examiner* — Serkan Akar
*Assistant Examiner* — Jason P Gross
(74) *Attorney, Agent, or Firm* — Morrison & Foerster LLP

(57) ABSTRACT

A surgical tool for an endoscopic procedure includes a proximal portion and a distal portion configured for at least partial insertion in a surgical cavity of the patient during the endoscopic procedure, at least a portion of the distal portion being made of a polymer and comprising at least one fiducial marker formed by laser marking of the polymer for detection by an endoscopic imaging system.

21 Claims, 12 Drawing Sheets

(56) References Cited

U.S. PATENT DOCUMENTS

| | | | | |
|---|---|---|---|---|
| 2018/0071032 | A1* | 3/2018 | de Almeida Barreto | G06T 19/006 |
| 2021/0121053 | A1* | 4/2021 | Sidlesky | A61B 90/36 |
| 2022/0108475 | A1* | 4/2022 | Nir | A61B 90/39 |
| 2022/0280245 | A1* | 9/2022 | Lent | A61B 1/0005 |
| 2023/0000566 | A1* | 1/2023 | Bell | A61B 34/71 |
| 2023/0102358 | A1* | 3/2023 | Shelton, IV | G06V 10/803 600/426 |
| 2024/0185432 | A1* | 6/2024 | Polchin | G06V 10/82 |
| 2025/0186162 | A1* | 6/2025 | Torrie | A61B 17/8695 |

OTHER PUBLICATIONS

Liu et al. “Hybrid electromagnetic—ArUco tracking of laparoscopic ultrasound transducer in laparoscopic video.” Journal of Medical Imaging 8.1 (2021): (Year: 2021).*

Nwoye et al. (Mar. 3, 2022). “Rendezvous: Attention Mechanisms for the Recognition of Surgical Action Triplets in Endoscopic Videos,” located at https://doi.org/10.48550/arXiv.2109.03223, 23 pages.

* cited by examiner 500
506
504
520
503
502
510
508
514
512
522

SURGICAL TOOL INCLUDING A BLACK POLYMER DISTAL PORTION HAVING TRANSVERSE PLANAR SURFACES WITH LASER-MARKED FIDUCIAL MARKERS

CROSS-REFERENCE TO RELATED APPLICATIONS

This application claims the benefit of U.S. Provisional Application No. 63/502,026, filed May 12, 2023, the entire contents of which are hereby incorporated by reference herein.

FIELD

This disclosure generally relates to endoscopic imaging and, more particularly, to determining the position of surgical tools in endoscopic imaging based on fiducial markers disposed on the surgical tools.

BACKGROUND

Medical imaging involves the use of a high-definition camera, often coupled to an endoscope inserted into a patient to provide a surgeon with a clear and precise view within the body. In many instances, the video data collected at the camera will be transmitted to a display device that will render the video data collected onto a display so that the surgeon can visualize the internal area of the body that is being viewed by the camera. In many instances, the camera can serve as the eyes of the surgeon during the surgery, since the camera may provide the only view of the internal area of the patient. In many instances, the surgeon may depend on the camera to perform procedures in the internal area of the patient, using one or more tools that are specifically configured to aid the surgeon as they perform the medical procedure. The surgeon can view the imaging feed being displayed to them during a surgery to manipulate the tool and navigate the tool within the internal area of the patient.

Medical imaging data such as an endoscopic video feed and/or image can also be used by the surgeon to measure distances within the internal portion of a patient. For instance, if the scale of the image shown on the screen is known, as well as depth information, then the surgeon can use the endoscopic imaging data to measure distances of the internal portion of the patient in either two dimensions, three dimensions, or both. In the instance where sufficient information about an endoscopic image exists to measure distances or determine the position of an object in the image, the tools that are used in the endoscopic procedure can be used to measure distances and or determine the position of a feature in the internal area of the patient. A pointer tool is an example of a tool that can be used by a surgeon during an endoscopic procedure. A pointer tool can include a tip that the surgeon can use to palpate the anatomy of the patient and act as the "fingers" of the surgeon during an endoscopic surgery. Thus, the surgeon can use the tip of a pointer tool to measure distance in the anatomy or otherwise determine the precise three- or two-dimensional location of a feature of the patient's anatomy. For instance, the end of the tip can be used to delineate two end points of a measurement. The tip of the point tool can be used to indicate a start point and an end point of a measurement. With respect to determining the location of a feature, the tip of the pointer tool can be placed at a feature of interest, and the position of the tip can be recorded.

However, in order to use the pointer in the manner described above, the endoscopic imaging system, and more specifically the device processing the imaging data, must be able to recognize the location of the tip in the endoscopic imaging data. The imaging data can be represented by a plurality of digital pixels, and thus in order to determine the tip of the tool in the image, the device must first determine the presence of the pointer tool in the imaging data, and then determine the exact pixels that are associated with the tip of the pointer tool. Determining the position of the tip can be challenging in its own right, but this challenge can be made even more complex and difficult to overcome when the tip gets obscured or hidden from the view of the camera during the surgical procedure. For instance, if the tip gets buried in the anatomy of the patient such that it is not visible in the endoscopic images, then determining its two- or three-dimensional position can be difficult.

SUMMARY

According to an aspect, a surgical tool includes a polymer portion that includes at least one fiducial marker formed using a laser marking process that produces regions that have prominent contrast. For example, the laser marking process can use a UV or green laser to transform regions of a dark color polymer to a lighter color, such as white. By creating a fiducial marker that has lighter and darker regions with prominent contrast, the fiducial marker can be easily detected in endoscopic images by an image processing system.

According to an aspect, a surgical tool for an endoscopic procedure includes a proximal portion (e.g., that can be grasped by a user for manipulating the surgical tool within a surgical cavity during the endoscopic procedure) and a distal portion configured for at least partial insertion in a surgical cavity of the patient during the endoscopic procedure, where at least a portion of the distal portion is made of a polymer and includes at least one fiducial marker formed by laser marking of the polymer for detection by an endoscopic imaging system.

The at least one fiducial marker may include lighter regions and darker regions, the lighter regions having been laser marked, the darker regions not having been laser marked. A width of at least one darker region may be the same as a width of at least one lighter region. A size of the at least one fiducial marker may be less than 3 mm×3 mm. The at least one fiducial marker may be, for example, an ArUco marker.

The at least one fiducial marker may include at least first and second fiducial markers, wherein the first fiducial marker is oriented transversely relative to the second fiducial marker. The at least one fiducial marker may include a plurality of fiducial markers disposed about a longitudinal axis of the distal portion. The at least one fiducial marker may include a first set of fiducial markers located distally of a second set of fiducial markers.

The polymer may be or include Delrin, Radel, Acrylonitrile Butadiene Styrene (ABS), an acetal copolymer, and/or nylon. The polymer may include a carbon colorant.

The surgical tool may be a pointer tool.

The distal portion of the surgical tool may include a distal end of the surgical tool, and the distal portion may be coupled to a shaft of the surgical tool, the shaft extending from the proximal portion to the distal portion. The distal portion may be made entirely of the polymer.

The at least one fiducial marker may have been laser marked with a laser having a wavelength less than or equal to 2,100 nm. The laser may be an ultraviolet laser.

According to an aspect, a method of endoscopic imaging includes, at a computing system, receiving at least one endoscopic image that captures a surgical tool positioned in a surgical cavity, detecting in the at least one endoscopic image at least one fiducial marker formed by laser marking a polymer portion of the surgical tool and determining a position of at least a portion of the surgical tool in the surgical cavity based on the at least one fiducial marker.

The at least one fiducial marker may include a laser marked perimeter and determining the position of the at least a portion of the surgical tool may include determining a location of at least one corner of the laser marked perimeter.

The at least one fiducial marker may include lighter regions and darker regions, the lighter regions having been laser marked, the darker regions not having been laser marked, and wherein a width of at least one darker region is the same as a width of at least one lighter region. A size of the at least one fiducial marker may be less than 3 mm×3 mm. The at least one fiducial marker may be an ArUco marker.

The at least one fiducial marker comprises at least first and second fiducial markers, wherein the first fiducial marker is oriented transversely relative to the second fiducial marker.

The polymer portion may be formed of or include Delrin, Radel, Acrylonitrile Butadiene Styrene (ABS), an acetal copolymer, and/or nylon. The polymer portion may include a carbon colorant.

The surgical tool may be a pointer tool.

The polymer portion may include an entire distal end of the surgical tool.

The at least one fiducial marker may have been laser marked with a laser having a wavelength less than or equal to 2,100 nm. The laser may be an ultraviolet laser.

According to an aspect, a fixture for laser marking a surgical tool with at least one fiducial marker includes a shaft for mounting the fixture to a rotary actuator so that the shaft can be rotated about a longitudinal axis of the shaft; a first mount for mounting at least a portion of the surgical tool, the first mount having a first orientation with respect to the longitudinal axis of the shaft for aligning a first location of the at least a portion of the surgical tool with the longitudinal axis of the shaft so that a first plurality of fiducial markers can be marked at an array of positions at the first location of the at least a portion of the surgical tool by rotating the fixture via the rotary actuator; and a second mount for mounting the at least a portion of the surgical tool, the second mount having a second orientation relative to the longitudinal axis of the shaft that is different than the first orientation for aligning a second location of the at least a portion of the surgical tool with the longitudinal axis of the shaft so that a second plurality of fiducial markers can be marked at an array of positions at the second location of the at least a portion of the surgical tool by rotating the fixture via the rotary actuator.

The first orientation may be an aligned orientation with respect to the longitudinal axis of the shaft.

The first and second mounts may each include a cylindrical bore for receiving a cylindrical portion of the surgical tool. A longitudinal axis of a cylindrical bore of the first mount may be coaxial with the longitudinal axis of the shaft. A longitudinal axis of a cylindrical bore of the second mount may extend transversely to the longitudinal axis of the shaft. The longitudinal axis of the cylindrical bore of the second mount may extend at 45 degrees to the longitudinal axis of the shaft.

The first mount may be configured for positioning the first location of the at least a portion of the surgical tool at a first distance from the shaft and the second mount may be configured for positioning the second location of the at least a portion of the surgical tool at the first distance from the shaft.

It will be appreciated that any of the variations, aspects, features, and options described in view of the systems apply equally to the methods and vice versa. It will also be clear that any one or more of the above variations, aspects, features, and options can be combined.

BRIEF DESCRIPTION OF THE FIGURES

The invention will now be described, by way of example only, with reference to the accompanying drawings, in which.

DETAILED DESCRIPTION

Figure 1:
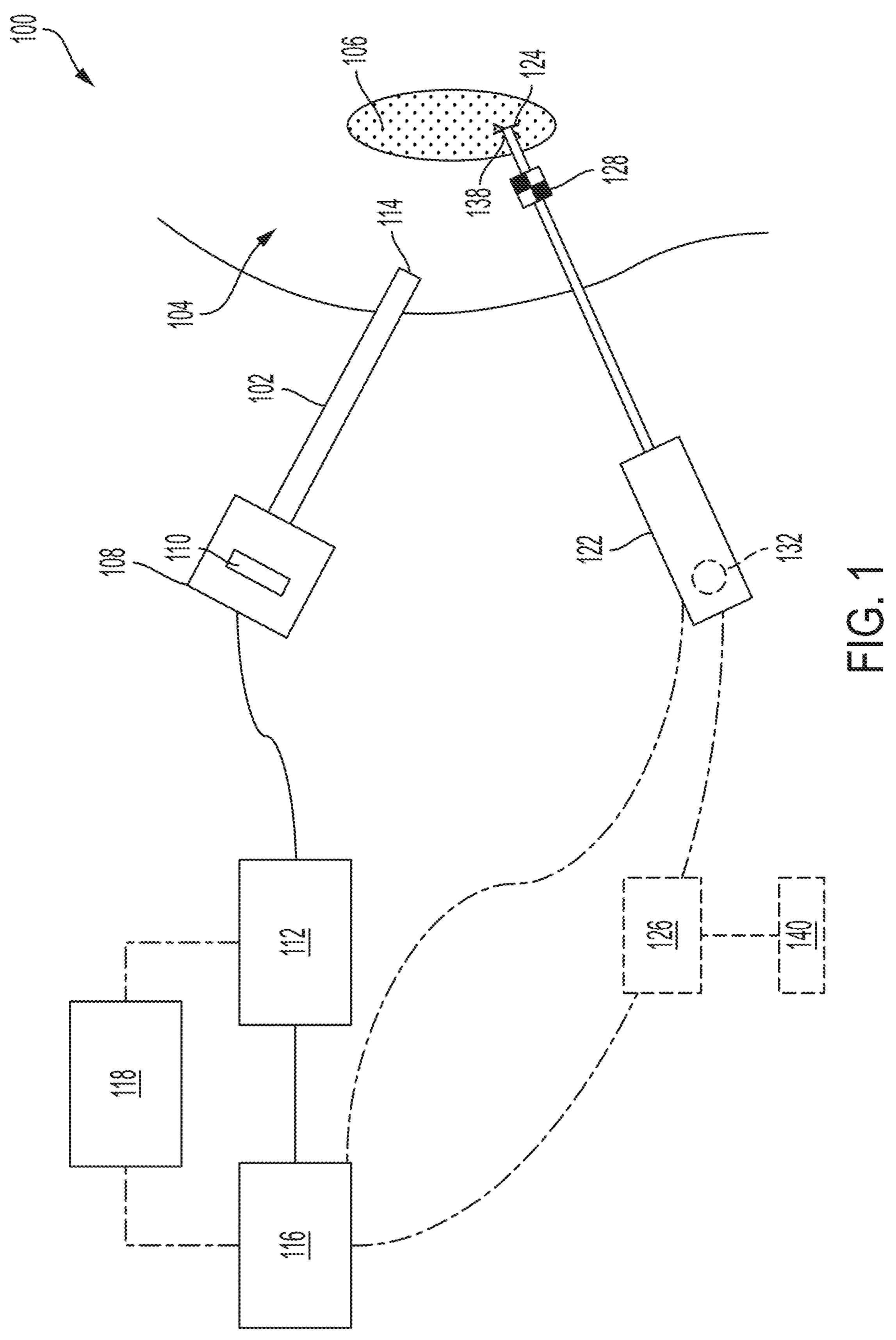
FIG. 1 illustrates an exemplary endoscopy system.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner, having combinations of all or some of the aspects described.

Described herein are systems, devices, and methods for detecting, by an image processing system, at least one fiducial marker of a surgical tool in endoscopic images during an endoscopic procedure on a subject. The detection of the fiducial marker can be used by the image processing system to determine the position and/or orientation of the surgical tool or a portion thereof based on one or more endoscopic images that capture the surgical tool. The determined position of the surgical tool can be used by the image processing system for any number of different purposes, including, for example, to provide a graphical indication of the location of the tissue of interest proximate a distal end of the surgical tool in one or more endoscopic images displayed to a user, to track a particular location of the tissue of interest over an imaging session or portion of an imaging session, and/or to generate one or more measurements associated with the location of the surgical tool relative to the tissue of interest.

The fiducial marker can be formed in a way that provides prominent contrast between different regions of the fiducial marker, so that the fiducial marker may be easily detected by an imaging processing system. For example, the fiducial marker may have a pattern of light- and dark-colored regions and the fiducial marker may be formed in a way that provides prominent contrast between the light- and dark-colored regions. In some examples, the fiducial marker is formed on a dark-colored polymer and the light- and dark-colored regions of the fiducial marker are formed by using a laser marking process to transform regions of the dark-colored polymer into light-colored regions, with the adjacent unmarked dark-colored polymer regions forming the dark-colored regions. The polymer can be, for example, Delrin, Radel, Acrylonitrile Butadiene Styrene (ABS), an acetal copolymer, or nylon and can include one or more additives that give the polymer a dark color, and the laser marking process can use an ultraviolet laser, a visible light laser (such as a green laser), a fiber laser, or any other suitable laser to mark the polymer, resulting in light and dark regions with prominent contrast.

The surgical tool can be a pointer tool that has a pointed distal end that a user may place adjacent to a location of the tissue of interest to indicate in endoscopic images the location of the tissue of interest. The distal portion of the pointer tool may be a polymer that has one or more fiducial markers formed on it. The one or more fiducial markers may be detected in one or more endoscopic images by an image processing system, the position of the one or more fiducial markers may be determined by the image processing system, and the location of the tip of the pointer tool may be determined based on predefined positional relationships between the one or more fiducial markers and the tip of the pointer tool.

In the following description of the various examples, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating," or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general-purpose computer selectively activated or reconfigured by a computer program stored in the computer. Such a computer program may be stored in a non-transitory, computer-readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application-specific integrated circuits (ASICs), or any type of media suitable for storing electronic instructions, and each connected to a computer system bus. Furthermore, the computing systems referred to in the specification may include a single processor or may be architectures employing multiple processor designs, such as for performing distinct functions or for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present disclosure as described herein.

FIG. 1 illustrates an exemplary endoscopy system. System 100 includes an endoscope 102 for insertion into a surgical cavity 104 for imaging tissue 106 within the surgical cavity 104 during a medical procedure. The endoscope 102 may extend from an endoscopic camera head 108 that includes one or more imaging sensors 110. Light reflected and/or emitted (such as fluorescence light emitted by fluorescing targets that are excited by fluorescence excitation illumination light) from the tissue 106 is received by the distal end 114 of the endoscope 102. The light is propagated by the endoscope 102, such as via one or more optical components (for example, one or more lenses, prisms, light pipes, or other optical components), to the camera head 108, where it is directed onto the one or more imaging sensors 110. In one or more examples, one or more filters (not shown) may be included in the endoscope 102 and/or camera head 108 for filtering a portion of the light received from the tissue 106 (such as fluorescence excitation light).

The one or more imaging sensors 110 generate pixel data that can be transmitted to a camera control unit 112 that is communicatively connected to the camera head 108. The camera control unit 112 generates a video feed from the pixel data that shows the tissue being viewed by the camera at any given moment in time. In one or more examples, the video feed can be transmitted to an image processing unit 116 for further image processing, storage, display, and/or routing to an external device (not shown). The images can be transmitted to one or more displays 118, from the camera control unit 112 and/or the image processing unit 116, for visualization by medical personnel, such as by a surgeon for visualizing the surgical cavity 104 during a surgical procedure on a patient.

In one or more examples, the images generated by the system 100 described above can be used to create two-dimensional and/or three-dimensional maps of the internal anatomy of a patient. For instance, in one or more examples, the images are represented on a screen in two dimensions and thus can be represented using an (x,y) coordinate system, in which each location or point in the internal portion can correspond to a specific (x,y) coordinate. Even as the camera is repositioned throughout the surgery, the images created by the camera can be stitched together to create an overall two-dimensional mapping of the internal anatomy of the patient, such that no two points in the internal anatomy of the patient viewed by the camera will have the same (x,y) coordinate.

In one or more examples, the two-dimensional model created by the endoscopic video feed during a surgical procedure can be transformed into a three-dimensional model by adding depth information to the two-dimensional model. In one or more examples, depth information pertaining to endoscopic image or endoscopic video feed can be obtained by using hardware-based methods, such as employing the use of stereo cameras, time of flight sensors, etc. Additionally or alternatively, the depth information can be acquired algorithmically, for instance, by using a structure from motion process in conjunction with a camera to acquire depth information. Additionally or alternatively, the depth information can be acquired using external data acquired on the patient such as magnetic resonance images (MRIs), etc. Similar to two-dimensional mappings, the above techniques can be employed to create a three-dimensional map of the internal anatomy of the patient, such that every point visualized by an endoscopic camera can have a unique (x, y, z) coordinate.

The two- and/or three-dimensional mappings discussed above can be used to generate two- or three-dimensional measurements within the internal portion of the patient. For instance, the distance between two (x, y, z) points within the patient's internal anatomy can be measured in real-time using the three-dimensional mappings acquired using the systems and processes described above. In order to take a measurement, a surgeon may need to accurately identify the start point and end point of such a measurement, and/or the contours of the measurement to be taken. In one or more examples, a surgeon can utilize a pointer tool 122 to point to the specific points in the internal anatomy of a patient to use in a two- or three-dimensional measurement that is being taken using images taken from an endoscopic imaging device. In one or more examples, the pointer tool 122 can include a pointer that has a tip 138 located at an end of the pointer tool 122 that can be captured in imaging data generated by the camera head 108 and used by the surgeon to mark or point to a specific point of interest 124 in the imaging data of the patient's internal anatomy. One challenge associated with using a pointer tool to mark points in a patient's anatomy is identifying the precise location of the tip in the endoscopic image.

In order to use the pointer as a "marking" device, an image processing system, such as image processing unit 116, must determine where the tip of the pointer to be used to mark is located. The task of finding the tip of the pointer tool can be even more complicated when the tip is obscured by a patient's anatomy (for instance, by being buried in the patient's tissue) or otherwise not completely visible in the endoscopic image due to other occlusions or obfuscations. To this end, pointer tool 122 can be specifically configured to allow for easy and robust identification of the tip 138 of a pointer tool by an image processing system, such as image processing unit 116, for the purposes of marking a portion of a patient's anatomy or any other context in which the precise two- and/or three-dimensional location of the tip may be required. The pointer tool 122 can include features that enable an image processing system to acquire the location of the tip 138 regardless of the orientation the pointer tool 122 is in, and regardless of whether the tip 138 is visible in the image or not. For example, the pointer tool 122 can include one or more fiducial markers 128 that can be captured in imaging data and used by an image processing system, such as image processing unit 116, to not only identify the pointer tool 122, but identify its orientation and identify the precise two- or three-dimensional location of the tip of the tool, which the image processing system can use to take two- or three-dimensional measurements.

In some examples, the pointer tool 122 can include one or more buttons 132 or other user interface that a user can use to instruct the image processing unit 116 to determine the position the location of interest 124 based on the position of the tip 138 of the pointer tool 122. For example, the user can position the pointer tool 122 at or near the location of interest 124 and press the button 132 on the pointer tool 122 to indicate that the image processing unit 116 should determine the position of the location of interest 124. The pointer tool 122 can be directly connected to the image processing unit 116 or can be connected to a tool controller 126 configured to receive input from the pointer tool 122. The tool controller 126 can receive a signal from the pointer tool 122 responsive to a button press. The tool controller 126 can send a notification to the image processing unit 116 indicative of the user's instruction to determine the location of interest 124. The image processing unit 116 can then analyze one or more endoscopic images to determine the three-dimensional position of the location of interest 124. The user can reposition the pointer tool 122 and provide another button press to control the system 100 to determine a new location of interest based on the repositioned position of the pointer tool 122. This can be repeated any number of times by the user. In some examples, the pointer tool 122 may include a memory storing identifying information for the pointer tool 122 that the pointer tool 122 may provide to the image processing unit 116 and/or the tool controller 126 so that the imaging processing unit 116 and/or the tool controller 126 can determine how to interpret communications from the pointer tool 122.

In some examples, the pointer tool 122 does not include any user input features. Instead, the pointer tool 122 may include a shaft extending from a simple handpiece or simply a shaft grasped at one end by a user. In such examples, a user input instructing the image processing unit 116 to determine the three-dimensional position of the location of interest 124 can be provided via any other user interface of system 100, including, for example, a voice control system, a remote control, another tool, or a foot switch. For example, the tool controller 126 may include or be connected to a user interface 140, such as a foot switch, to which a user may provide an input to instruct the image processing unit 116 to determine the three-dimensional position of the location of interest 124. Optionally, the tool controller 126 and user interface 140 can be used to communicate with tools other than the pointer tool 122, such as a cutting tool, and the tool controller 126 can change how it responds to inputs to the user interface 140 based on which tool is being used. The image processing unit 116 may detect the presence of the pointer tool 122 in imaging data, such as by detecting the fiducial marker 128, and may inform the tool controller 126 that the pointer tool 122 is being used. The tool controller 126 may then respond to inputs to the user interface 140 based on configuration data associated with the pointer tool 122 (instead of, for example, configuration data associated with a cutter). Optionally, the configuration data may be customizable based on user preferences so that, for example, mappings of user interface 140 inputs to tool controller 126 outputs can be different for different users.

Although FIG. 1 shows a pointer tool 122 and the examples below often refer to a pointer tool, it is to be understood that the principles described herein are applicable to any surgical tool, including cutting tools, drill guides, and any other surgical tool that can be placed in the surgical cavity within a field of view of an endoscopic camera.

Figure 2:
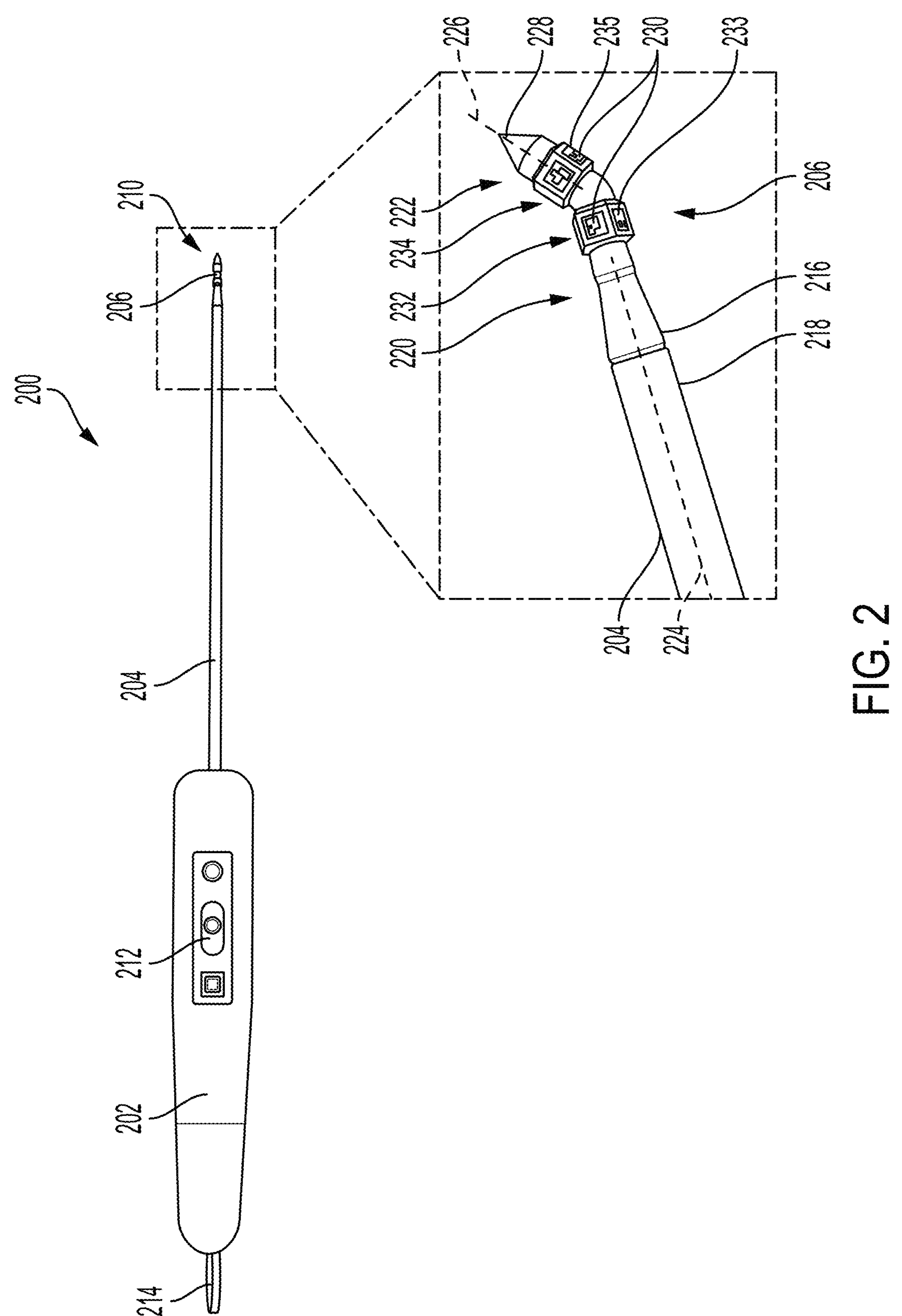
FIG. 2 shows an enlarged view of a distal portion of an exemplary pointer tool.

An example of pointer tool 122 is illustrated in FIG. 2. The pointer tool 200 shown in FIG. 2 includes a handle 202 that is grippable by a user for manipulating the pointer tool 200 during an endoscopic procedure, a shaft 204 extending distally from the handle 202 for at least partial insertion into a surgical cavity, and a pointer 206 that comprises the distal end 210 of the pointer tool 200. The distal end 210 of the pointer tool 200 is located inside of the surgical cavity so as to be visible in endoscopic images of the surgical cavity. The handle 202 may include one or more buttons 212 and a cable 214 to transmit signals from buttons 212 (e.g., button presses) to a computing device, such as image processing unit 116 of system 100 of FIG. 1.

FIG. 2 shows an enlarged view of a distal portion of the pointer tool 200. The pointer 206 is coupled at its proximal end 216 to the distal end 218 of the shaft 204. The pointer 206 may be coupled in any suitable fashion, including via a threaded engagement, a press fit engagement, by being overmolded onto the shaft 204 and/or by being adhesively affixed to the shaft 204. In some examples, the pointer 206 and shaft 204 are formed as a single piece, such as a single piece of machined metal or polymer or a single piece of injection-molded polymer.

The pointer 206 includes a first portion 220 that is aligned with the shaft 204 and a second portion 222 that is distal of the first portion 220, extending transversely to the first portion 220 (e.g., at 45 degrees). That is, the first portion 220 is aligned with a longitudinal axis 224 of the shaft 204 and the second portion 222 has a longitudinal axis 226 that extends at an angle to the longitudinal axis 224 of the shaft 204. The second portion 222 includes a pointed tip 228 that may facilitate a user pointing to a location of interest within a surgical cavity.

The pointer 206 includes at least one fiducial marker 230. In the illustrated embodiment, the pointer 206 includes multiple fiducial markers arranged in two sets of fiducial markers. A first set 232 of fiducial markers is located on a corresponding set of surfaces 233 of the first portion 220 of the pointer 206 and a second set 234 of fiducial markers is located on a corresponding set of surfaces 235 of the second portion 222 of the pointer 206. The surfaces 233 and/or 235 may be flat surfaces or may be curved surfaces or a combination thereof. The first set 232 of fiducial markers includes a plurality of fiducial markers that are disposed around the longitudinal axis 224 of the shaft 204 and the second set 234 of fiducial markers includes a plurality of fiducial markers that are disposed around the longitudinal axis 226 of the second portion 222.

The pointer 206 can be a single component formed of a metal or a polymer or can be an assembly of components formed of one or more metals, one or more polymers, or a combination of metals and polymers. Examples of suitable polymers that may be used for the pointer 206 include Delrin, Radel, ABS, an acetal copolymer, or nylon. In some examples, pointer 206 is a single piece made entirely of polymer, such as entirely of Delrin, Radel, ABS, an acetal copolymer, or nylon. In some examples, pointer 206 is a metal, such as aluminum or stainless steel, which may be integrally formed with the shaft 204 or assembled to the shaft 204. In some examples, pointer 206 includes a metal portion onto which one or more polymer components are mounted, with the fiducial markers 230 being formed on the polymer components. For example, one or more rings of polymer onto which the fiducial markers 230 are formed may be pressed onto a metal piece to form the pointer 206. In some examples, the polymer comprises a heat shrink that is heat shrunk onto the pointer 206, and the fiducial markers 230 are formed on the heat shrink. Heat shrinking may be applied to a curved surface such that the fiducial markers 230 are formed on the curved surface. Forming the fiducial markers 230 on a curved surface may have the benefit of reducing glare from illumination within the surgical cavity, which can improve automatic detection of the fiducial markers 230. In some examples, a paint or finish (e.g., matte paint or matte finish) is applied to one or more flat or curved surfaces and the fiducial markers 230 are formed on the paint or finish. In some examples, the pointer 206 or portion(s) of the pointer 206 (onto which the fiducial markers 230 are formed) is made of a dark-colored polymer, such as a polymer dyed with a colorant. In some examples, the colorant is a carbon colorant that may result in the polymer being black. Other colorants may be used to achieve other colors, including, for example, dark gray, dark green, dark blue, dark red, etc. In some examples, the pointer 206 is a metal that has a dark color, such as an anodized aluminum (e.g., a black anodized aluminum).

Figure 3:
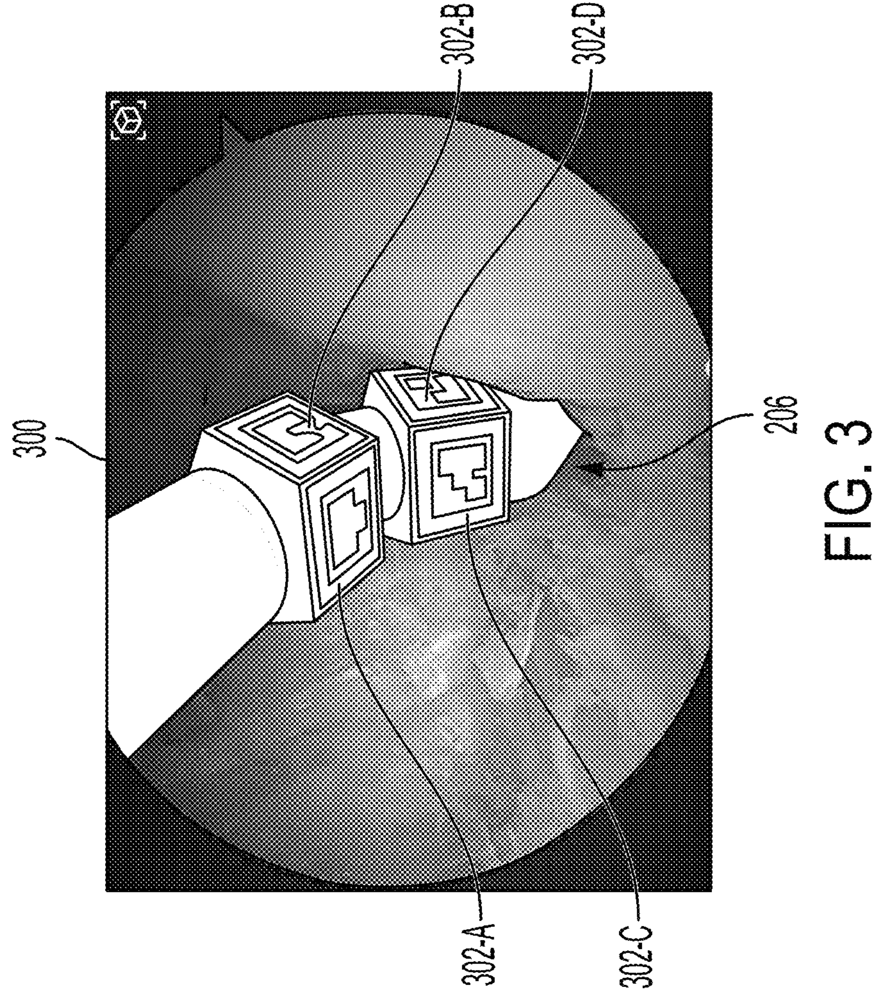
FIG. 3 illustrates an exemplary endoscopic image that captures a pointer of an exemplary pointer tool.

The arrangement of the fiducial markers 230 can help ensure that at least one fiducial marker is not only visible to the endoscopic camera at any given time during an endoscopic procedure, but that at least one fiducial marker is also oriented such that its surface normal is more parallel with the optical axis of the endoscopic camera relative to one or more other fiducial markers so that the fiducial marker is more visible than the one or more other fiducial markers and, thereby, more easily detected by an image processing system than the one or more other fiducial markers. FIG. 3 illustrates an exemplary endoscopic image 300 that captures the pointer 206. Three fiducial markers 302-A, 302-B, and 302-C are completely visible in the endoscopic image 300 and one fiducial marker 302-D is partially visible. Because of the different positions and orientations of the fiducial markers 302-A-D on the pointer 206, there is at least one fiducial marker (e.g., fiducial marker 302-C) that is more aligned with the optical axis of the endoscopic camera within the endoscopic image 300 and, therefore, more easily detected (e.g., than fiducial markers 302-A, 302-B, and 302-D) by an image processing system. To help ensure that at least one fiducial marker is visible in an endoscopic image despite the orientation of the pointer 206, each fiducial marker can be oriented transversely relative to at least one other fiducial marker. For example, fiducial marker 302-A is oriented transversely to fiducial marker 302-B and 302-C, meaning that a plane that comprises fiducial marker 302-A intersects, at an angle, a plane that comprises fiducial marker 302-B and intersects, at an angle, a plane that comprises fiducial marker 302-C.

Another aspect of detectability of a fiducial marker in an endoscopic image is the clarity of the fiducial marker. The fiducial marker may be formed of a pattern of light and dark regions. For example, the fiducial marker can be an ArUco marker that has a pattern of light squares and dark squares within a light border. Detectability of the fiducial marker may be a function of the contrast between the regions, the reflectivity of the regions, and/or the relative sizes of the regions. For example, light and dark regions that have low contrast may be difficult to differentiate by an image processing system, potentially leading to no detectability or to incorrectly detecting a light region as a dark region. Light and dark regions that have high reflectivity may be difficult to detect due to oversaturation in the image caused by the endoscopic imaging light reflecting off of the fiducial marker. Additionally, light and dark regions that are not sufficiently uniform in size may be difficult to detect by an image processing system that is configured to detect regions of similar size.

Figure 4A:
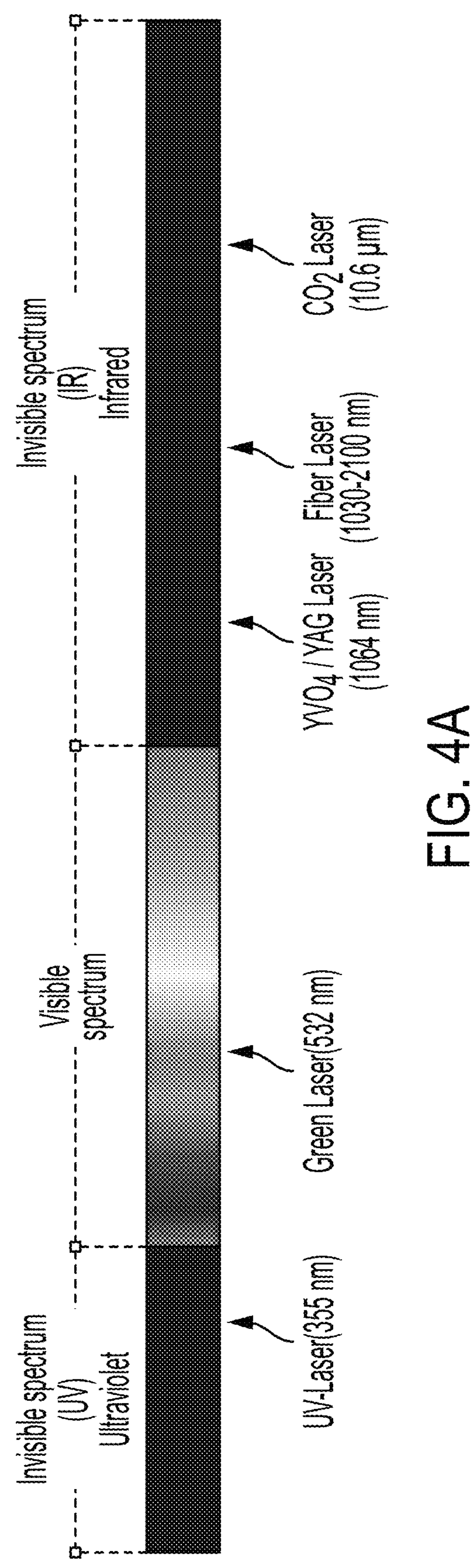
FIG. 4A illustrates different exemplary types of laser technology that may be used for generating fiducial markers on surgical tools.

A fiducial marker may be formed on the pointer 206 by a process that provides prominent contrast of the fiducial marker in endoscopic images. The fiducial marker may be formed by a laser marking process and the type of laser marking process, as well as the material for the pointer, may affect the contrast, reflectivity, and relative sizes of the regions. FIG. 4A illustrates different types of laser technology that may be used for generating the fiducial markers, including lasers that generate ultraviolet (UV) light, lasers that generate visible light, such as green light lasers, and lasers that generate infrared (IR) light, such as YAG lasers, fiber lasers, and $CO_2$ lasers. In some examples, a laser having a wavelength less than or equal to 2,100 nm may be used to form fiducial markers. In some examples, a laser having a wavelength of at least 355 nm may be used to formed fiducial markers.

Figure 4B:
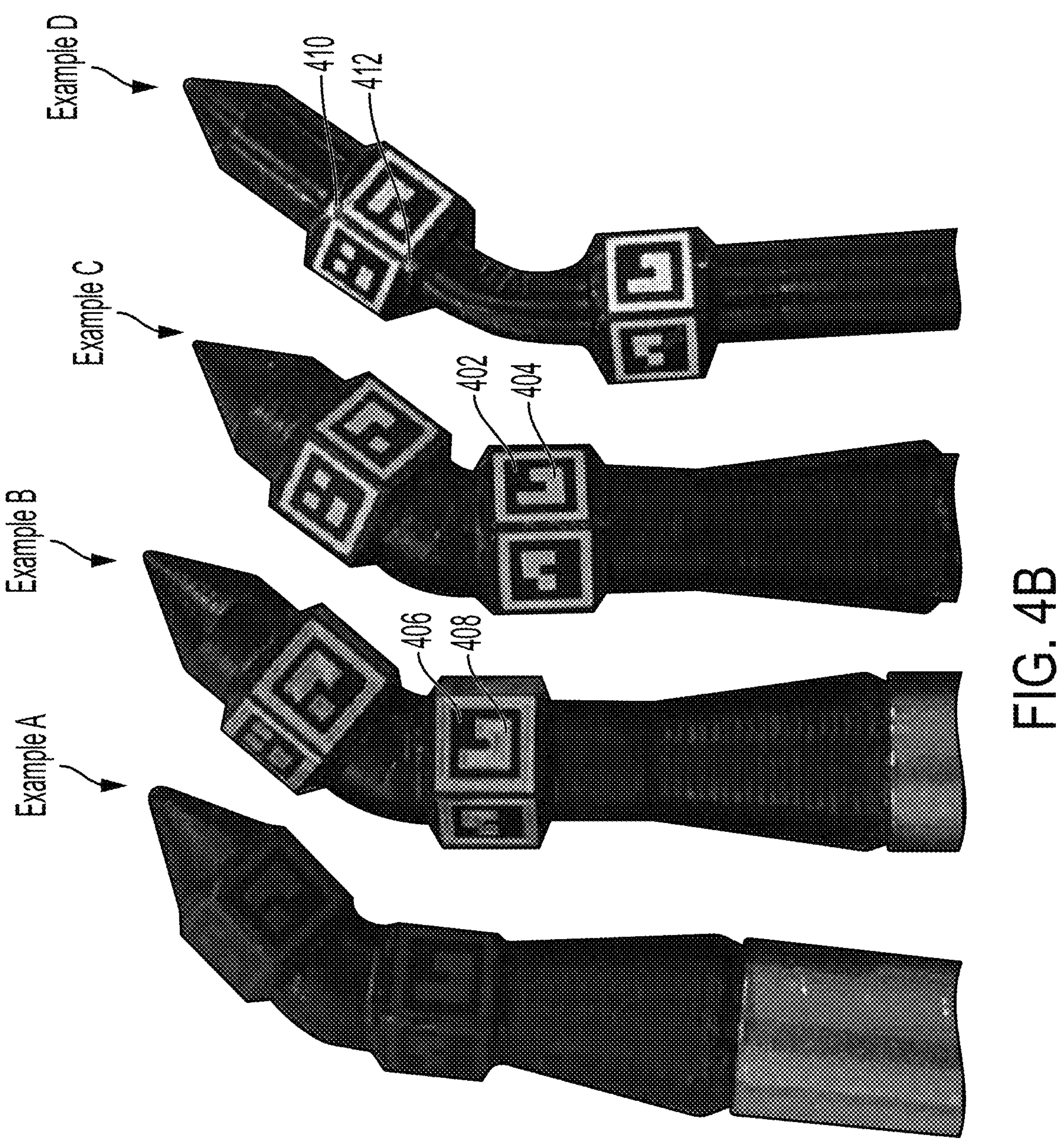
FIG. 4B illustrates examples of laser marking fiducial markers on different materials using different types of lasers.

FIG. 4B illustrates examples of laser marking fiducial markers on different materials using different types of lasers. In the illustrated examples, the fiducial markers are ArUco markers that have a pattern of light squares and dark squares within a light border. Example A is a black Radel polymer that was laser marked by a fiber laser, example B is black Delrin polymer that was laser marked by a fiber laser, example C is a black Delrin polymer that was laser marked with a UV laser, and example D is a black anodized aluminum that was laser marked with a fiber laser.

A comparison of the four examples of pointers shown in FIG. 4B illustrates effects that both the material and laser marking process may have on the clarity of the fiducial marker. A comparison of examples A and B illustrates the effect that different materials may have when used with the same laser marking process. Laser marking black Delrin with a fiber laser, as in example B, provides more contrast between light and dark regions, as compared to laser marking black Radel with a fiber laser, as in example A. The contrast can be improved further by switching from a fiber laser marking process on black Delrin to a UV laser marking process on black Delrin, as in example C. The light regions of example C are white in color, while the light regions of example B are grayer in color. This white color provides prominent contrast with the black background provided by the black Delrin. The black color of the polymer can be created using a suitable colorant, such as a carbon additive.

An advantage of the UV laser marking process over the fiber laser marking process is that the sizes of the light and dark regions are more uniform. For example, the widths of the dark region 402 and adjacent light region 404 of example C (UV laser marking of black Delrin) are more similar to each other than the widths of the corresponding dark region 406 and light region 408 of example B (fiber laser marking of black Delrin). This may be due to a fiber laser (example B) introducing more thermal energy into the material than a UV laser, resulting in melting of the material that reduces the ability to control the location of the edge between dark and light regions. The UV laser marking process for example C introduces less heat into the material, resulting in little or no melting and well-controlled edges. Thus, UV laser marking may be preferable for marking dark-colored polymers, such as black polymers. In some examples, green laser marking may provide results similar to the UV laser marking of example C. In some examples, the widths of the light and dark regions are the same (e.g., within 10% of one another). In some examples, the fiducial marker is an ArUco marker. The size of the ArUco marker may be less than 3 millimeters (about 0.12 inches) by 3 millimeters. For example, the size of the ArUco marker may be in a range of 2 millimeters (about 0.08 inches) by 2 millimeters to 2.75 (about 0.11 inches) millimeters by 2.75 millimeters. The ArUco maker may include an array of any suitable number of light and dark regions (also referred to herein as blocks) that fit within these dimensional ranges. For example, an ArUco marker may include a 2×2 array, 3×3 array, 4×4 array, 5×5 array, 6×6 array, 7×7 array, 8×8 array, etc., of blocks (any arrangement of light and dark blocks). So, for example, the size of each block may be in a range of about 0.25 millimeters (about 0.01 inches) by about 0.25 millimeters to about 1.5 millimeters (about 0.06 inches) by about 1.5 millimeters.

Example D, which is a laser marked black anodized aluminum, also demonstrates prominent contrast. However, the reflectivity of the black anodized aluminum is higher than the reflectivity of the black polymers of examples A-C, which can be seen by the reflection at locations 410 and 412. Such relatively high reflectivity may reduce the ability of an image processing system to detect the fiducial marker relative to a fiducial marker formed on a lower reflectivity polymer, such as Delrin or Radel.

Tables A and B below illustrate laser marking parameter values that may be used to form fiducial markers (such as ArUco markers having the light and dark region sizes listed above) on the various different materials in the tables. Table A shows exemplary laser marking parameter values for a fiber laser marking process and Table B shows exemplary laser marking parameter values for a UV laser marking process. The parameter terms used in these tables are defined as follows. “Fill Interval” is the distance between each scanline of the laser. “Laser Power” is the laser emission output as a percentage of full output. “Scan Speed” is the movement speed of the laser beam. Generally, the faster the scan speed is, the thinner (shallower in processing) the marking density, and the marking time will get shorter. “Pulse Frequency” is the laser oscillation frequency. Generally, the higher the pulse frequency is, the lower the energy per pulse. “Spot Variable” is the change in spot size (focal length). “Repetition” is the marking count (i.e., how many passes the laser will make).

TABLE A

| Fiber Laser Marker | | | | | | |
|---|---|---|---|---|---|---|
| | Laser Parameters | | | | | |
| Material | Fill Interval [mm] | Laser Power [%] | Scan Speed [mm/s] | Pulse Frequency [kHz] | Spot Variable | Repetition |
| Delrin (Black) | 0.06 | 75 | 5,500 | 100 | 20 | 2 |
| Radel (Black) | 0.06 | 75 | 5,500 | 80 | 20 | 2 |
| Nylon (Black) | 0.06 | 75 | 2,500 | 50 | 20 | 2 |
| ABS (Black) | 0.06 | 15 | 3,000 | 60 | −40 | 2 |
| Aluminum 6061 (anodized black) | 0.02 | 60 | 120 | 50 | −40 | 1 |

TABLE B

| UV Laser Marker | | | | | | |
|---|---|---|---|---|---|---|
| | Laser Parameters | | | | | |
| Material | Fill Interval [mm] | Laser Power [%] | Scan Speed [mm/s] | Pulse Frequency [kHz] | Spot Variable | Repetition |
| Delrin (Black) | 0.025 | 80 | 1,000 | 40 | −35 | 1 |
| Delrin 150 (Black) | 0.025 | 75 | 5,500 | 100 | 20 | 2 |
| Machined Acetyl Copolymer (Black) | 0.025 | 80 | 2,700 | 40 | −15 | 1 |

The values in the above tables include the following tolerances:

| Parameter | Tolerance |
|---|---|
| Fill Interval [mm] | ±0.005 |
| Laser Power [%] | ±5 |
| Scan Speed [mm/s] | ±200 |
| Pulse Frequency [kHz] | ±5 |
| Spot Variable | ±10 |
| Repetition | ±0 |

The combinations of materials and laser marking process in the tables above are merely exemplary. As noted previously, various examples can have fiducial markers formed by a laser having a wavelength less than or equal to 2,100 nm and/or a wavelength of at least 355 nm and may be formed on any suitable polymer, including Delrin, Radel, ABS, an acetal copolymer, nylon, or other similar polymer. Furthermore, various examples can have fiducial markers formed on a polymer that has any dark color that is capable of being transformed to a light color by a suitable laser marking process, such that light color regions have sufficiently prominent contrast with dark color regions to enable an image processing system to detect the dark and light regions.

Figure 5:
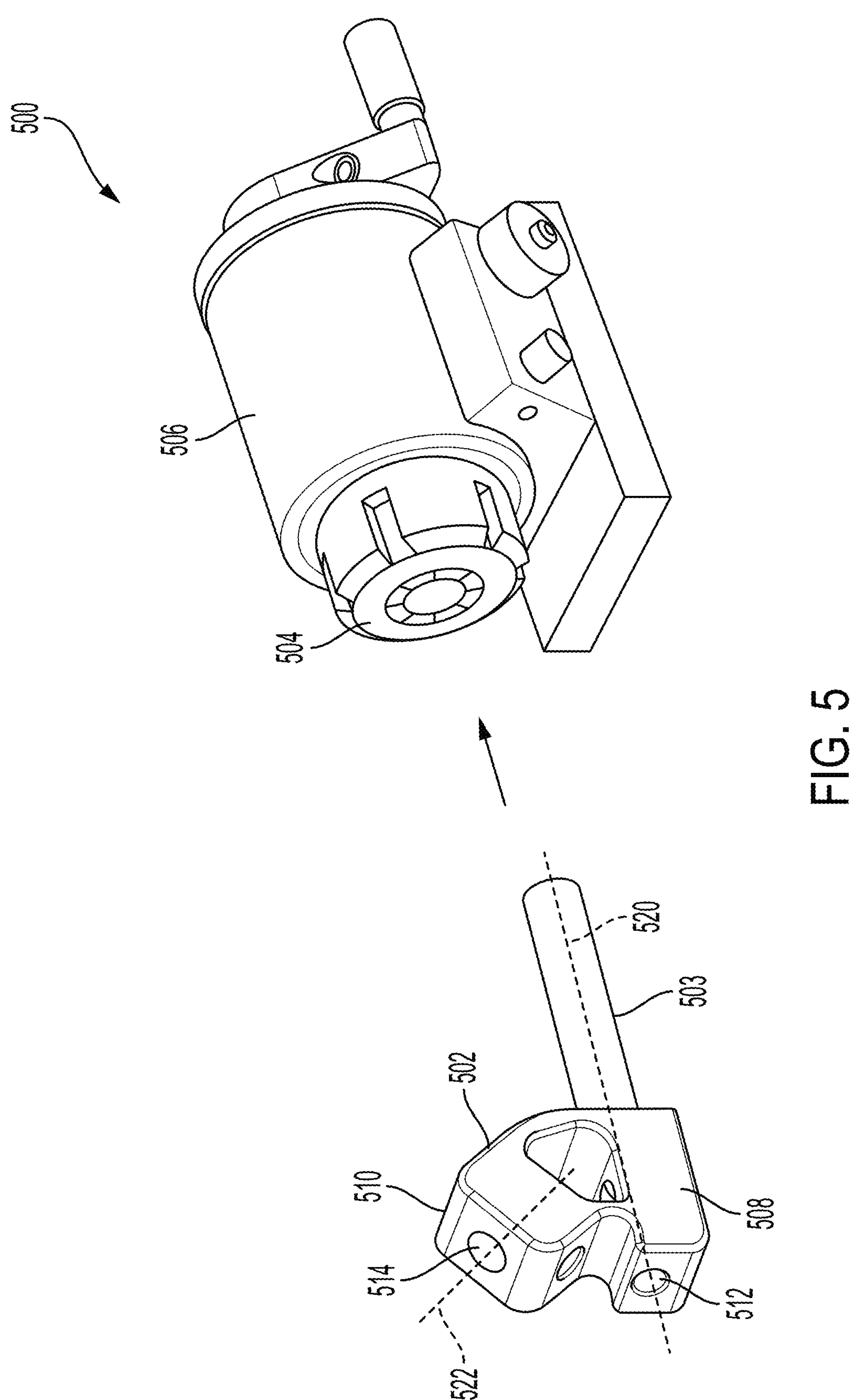
FIG. 5 illustrates an exemplary fixture for positioning various surfaces of a pointer for laser marking.

As explained above, the pointer tool may include a plurality of fiducial markers disposed at different locations and orientations on the pointer tool. To form the fiducial markers, the particular surface onto which a given fiducial marker is formed should be oriented perpendicularly to the marking laser. FIG. 5 illustrates an exemplary fixture assembly 500 for positioning pointer 206 in a plurality of different positions for laser marking the fiducial markers 230. The fixture assembly 500 can include fixture 502 that is mountable to a rotary positioner 506. In the example of FIG. 5, fixture 502 includes a shaft 503 that may be inserted into a chuck 504 of the rotary positioner 506. The rotary positioner 506 may be configured for setting the chuck 504 (and, thereby, the shaft 503 of fixture 502) into one or more predefined rotational positions.

Figure 6:
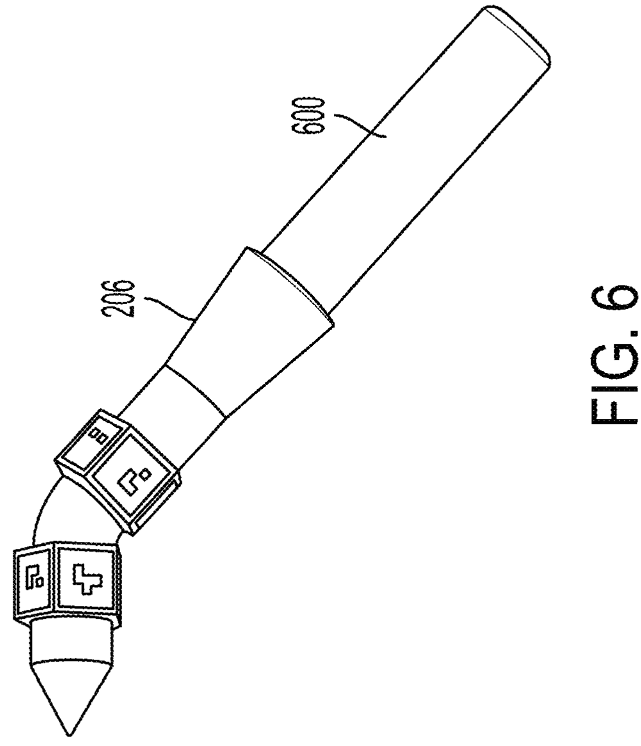
FIG. 6 illustrates an example of a configuration of a distal portion of a pointer of a pointer tool.

Fixture 502 may include two mounts 508 and 510 for mounting the pointer 206 in two different positions for marking the two different sets of fiducial markers. The two mounts 508 and 510 may include bores 512 and 514, respectively, for receiving a shank of the pointer 206. An exemplary shank 600 is illustrated in FIG. 6. The shank 600 of the pointer 206 can be used to couple the first portion 220 of the pointer 206 to the shaft 204 of the pointer tool 200, such as by insertion of the shank 600 into a bore of the shaft 204. The shank 600 and bores 512 and 514 may be configured such that the pointer 206 can be positioned in a predetermined orientation with respect to the fixture 502. For example, the shank 600 and bores 512 and 514 can have non-circular profiles or can be keyed. The shank 600 and bores 512 and 514 may be cylindrical. The shank 600 may be retained in the bores 512 and 514 in any suitable fashion, such as using a set screw that can be tightened onto the shank 600. Bore 512 of mount 508 can be aligned with a longitudinal axis 520 of the shaft 503 and bore 514 of mount 510 can extend transversely to the longitudinal axis 520 of the shaft 503 (i.e., its longitudinal axis 522 may intersect the longitudinal axis 520 of the shaft 503 at an angle, such as 45 degrees).

Figure 7B:
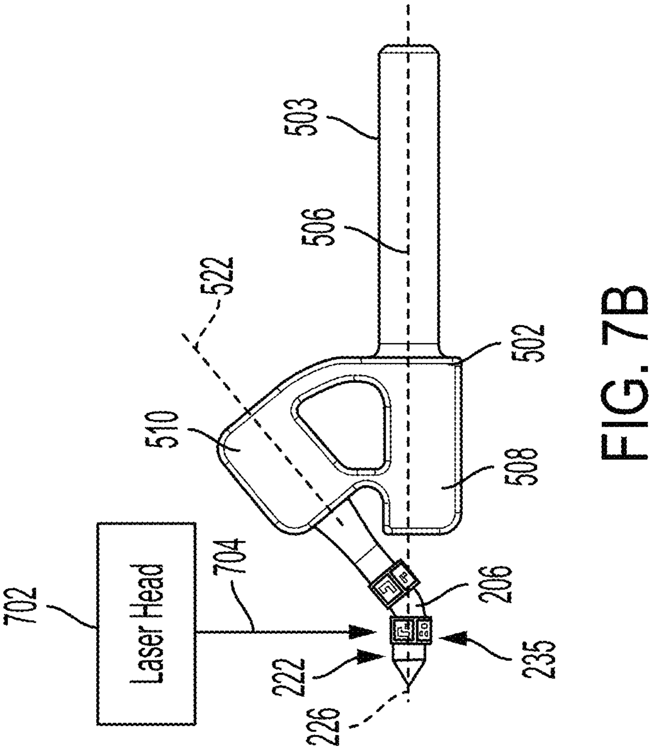
FIG. 7B illustrates the pointer mounted to the fixture at a second mounting location for marking a second set of fiducial markers.
Figure 7A:
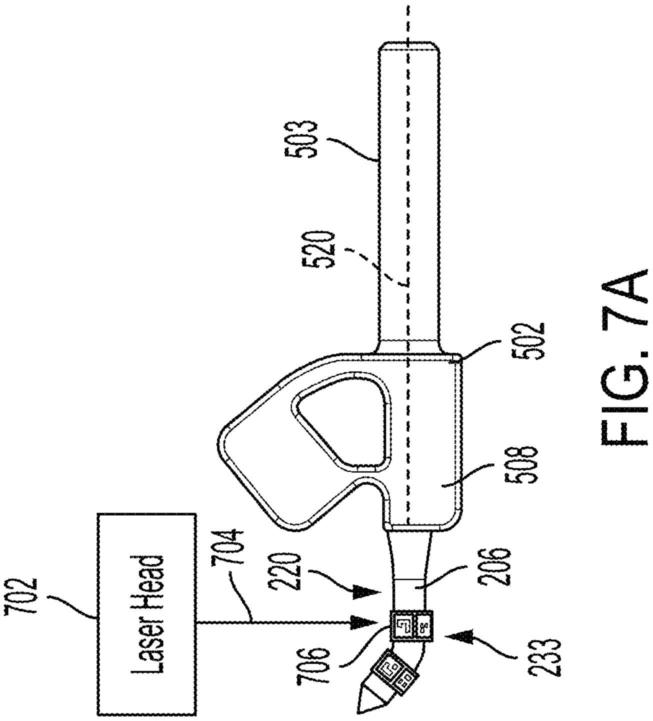
FIG. 7A illustrates an exemplary pointer mounted to the exemplary fixture of FIG. 5 at a first mounting location for marking a first set of fiducial markers.

FIG. 7A illustrates the pointer 206 mounted to mount 508 and FIG. 7B illustrates the pointer 206 mounted to mount 510. When mounted to mount 508, the first portion 220 of the pointer 206 is aligned with the longitudinal axis 520 of the shaft 503 of the fixture 502, which is also the rotational axis of rotary positioner 506 of FIG. 5. This positions the set of surfaces 233 of the first portion 220 of the pointer 206 in alignment with the longitudinal axis 520. The fixture 502 is positioned with respect to a laser head 702 such that a laser beam 704 is directed at the location of the first set of surfaces 233 of the first portion 220 of the pointer 206 in a direction perpendicular to the longitudinal axis 520. The rotary positioner 506 (see FIG. 5) can be set so that a first surface 706 of the first set of surfaces 233 is oriented perpendicularly to the direction of the laser beam 704. The laser beam 704 can then be used to laser mark the first surface 706. Once the fiducial marker has been laser marked on the first surface 706, the rotary positioner 506 of FIG. 5 can be used to rotate the fixture 502 about longitudinal axis 520 to a different rotational position in which a different surface of the first set of surfaces 233 is positioned beneath the laser head 702. Thus, by rotating the rotary positioner 506, each of the first set of surfaces 233 can be laser marked.

For laser marking the second set 234 of fiducial markers, the pointer 206 is mounted to mount 510, as shown in FIG. 7B. The bore 514 (see FIG. 5) of mount 510 has its longitudinal axis 522 oriented with respect to the longitudinal axis 520 such that the longitudinal axis 226 of the second portion 222 of the pointer 206 is aligned with the longitudinal axis 520, and the second set of surfaces 235 for receiving the second set 234 of fiducial markers is positioned in the same location that the first set of surfaces 233 was positioned when the pointer 206 was mounted to mount 508. Rotation of the fixture 502 using the rotary positioner 506 of FIG. 5 orients a different one of the set of surfaces 235 perpendicularly to the laser beam 704. Thus, fixture 502 can be used to accurately and repeatably position the pointer 206 in the correct positions for laser marking the sets of fiducial markers.

Figure 8:
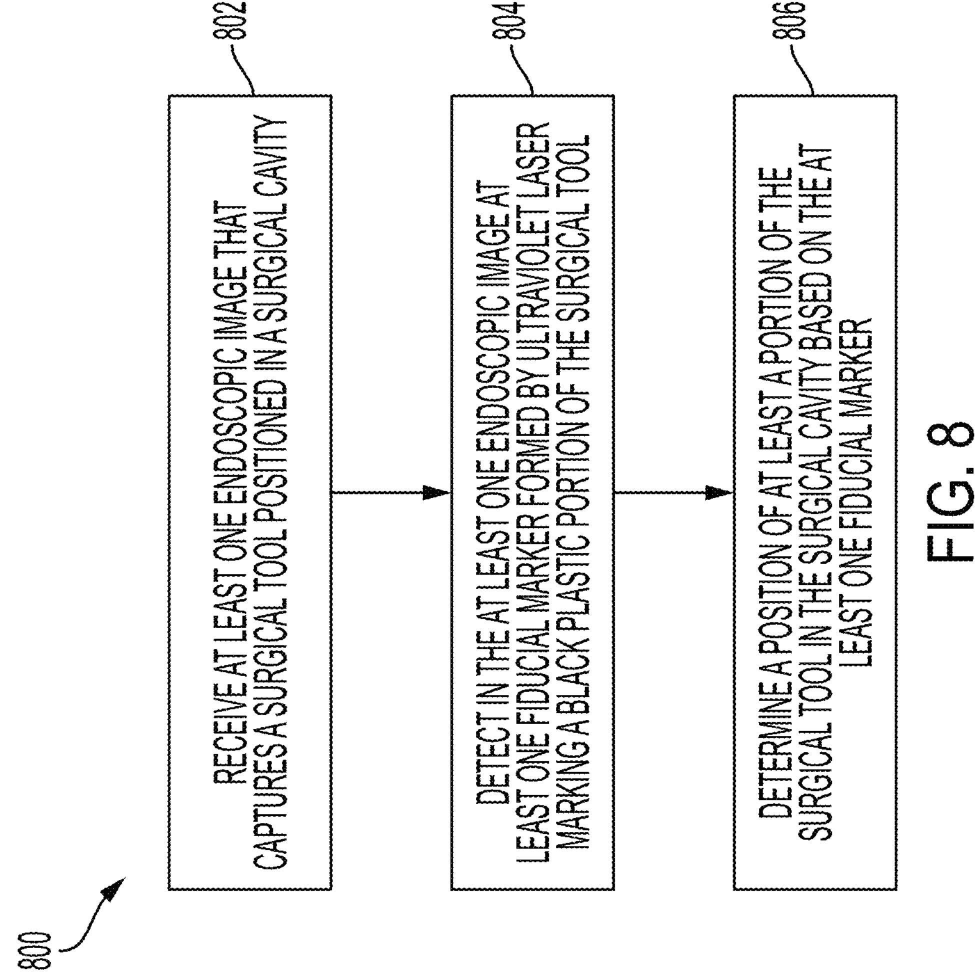
FIG. 8 illustrates an exemplary method for processing endoscopic images containing a surgical tool to determine a location of the surgical tool or a portion of the surgical tool during an endoscopic procedure on a subject.

FIG. 8 illustrates an exemplary method 800 for processing endoscopic images containing a surgical tool to determine a location of the surgical tool or a portion of the surgical tool during an endoscopic procedure on a subject. Method 800 can be performed by an image processing system, such as image processing unit 116 of system 100. Method 800 may be initiated by a user of the surgical tool, such by a user actuating a button 132 of pointer tool 122 of FIG. 1. Additionally or alternatively, method 800 can be performed continuously or automatically.

At step 802, at least one endoscopic image acquired by an endoscopic imaging system is received at the image processing system. For example, with reference to FIG. 1, image processing unit 116 may receive at least one endoscopic image (which can be one or more single snapshot images or one or more frames of a video) from camera control unit 112. The endoscopic image captures a surgical tool positioned within a surgical cavity. For example, the endoscopic image may capture pointer tool 122 positioned within surgical cavity 104.

At step 804, at least one fiducial marker of the surgical tool is detected in the endoscopic image. The surgical tool may have a polymer portion onto which the fiducial marker has been formed. For example, with reference to FIG. 2, the surgical tool can be pointer tool 200 that has a pointer 206 formed of a polymer and fiducial markers 230 laser marked on the polymer. The fiducial marker can have been formed by any laser marking process described herein, including by a UV laser marking process. The fiducial marker can have been formed by using a laser to transform regions of the polymer from a darker color to a lighter color, such as white, forming a pattern of light (e.g., white) and dark (e.g., black) regions. The image processing system may detect the fiducial marker by searching for and locating known visual patterns of the fiducial marker. In some variations, the fiducial marker is an ArUco marker, which includes an arrangement of light and dark blocks, the arrangement of which can uniquely identify a given fiducial marker relative to other fiducial markers of the surgical tool.

At step 806, the image processing system determines a position of at least a portion of the surgical tool based on the detected fiducial marker. The image processing system may determine a position and/or orientation of the fiducial marker and may determine the position of the surgical tool (or a portion thereof) based on predefined relationships between the fiducial marker and the surgical tool. For example, with reference to FIG. 2, the image processing system may determine the location of the tip 228 of the pointer tool 200 by accessing a database of predetermined positional relationships between the tip 228 of the pointer tool 200 and the fiducial marker(s) 230. The fiducial marker 230 can be an ArUco marker, and the database of predetermined positional relationships (which can be stored in the memory of the image processing system) can include a table of three-dimensional positions of the tip 228 of the pointer tool 200 relative to corners of a laser marked perimeter of the ArUco marker. The image processing system may determine a location of at least one corner of the laser marked perimeter of the ArUco marker in two- or three-dimensional space and may use the three-dimensional positional relationship between the corner of the laser marked perimeter for the fiducial marker as listed in the table to calculate the position of the three-dimensional position of the tip 228 of the pointer tool 200. The image processing system may do this for any of the fiducial markers that it is able to detect. The pointer tool 200 may include a plurality of fiducial markers that are each uniquely identifiable relative to the others (e.g., unique ArUco markers) and the table can include a set of three-dimensional positions associated with each of the plurality of fiducial markers 230.

Figure 10:
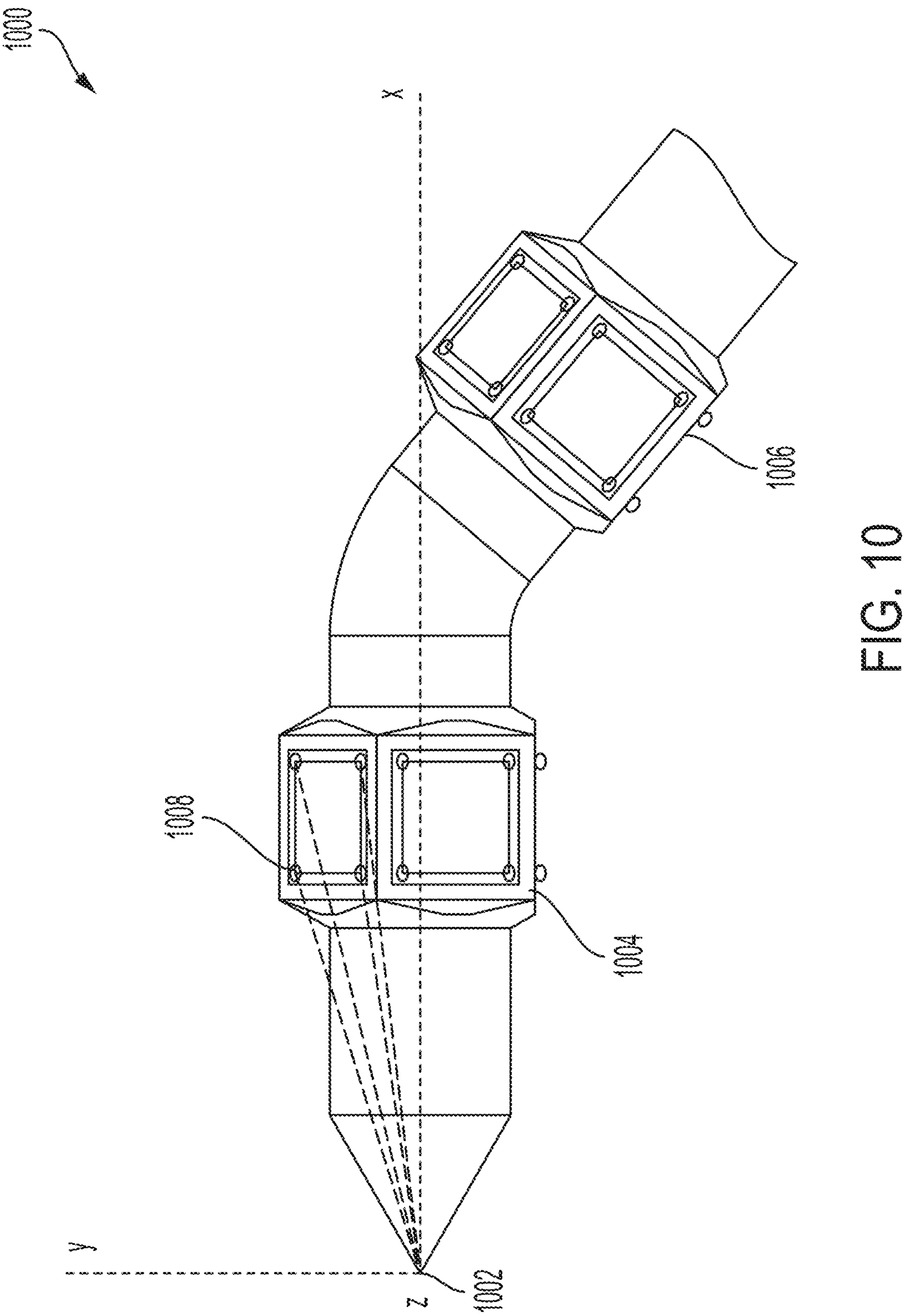
FIG. 10 illustrates an exemplary coordinate system for a pointer of an exemplary pointer tool.
Figure 11B:
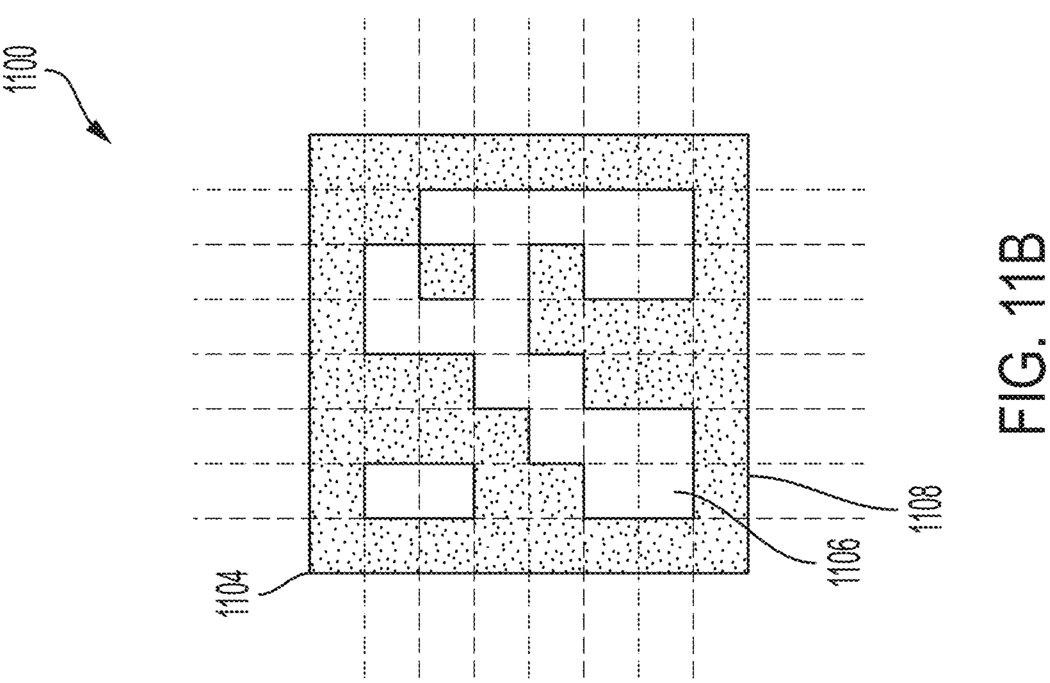
FIGS. 11A and 11B illustrate an exemplary ArUco marker that can be disposed on a pointer tool.
Figure 11A:
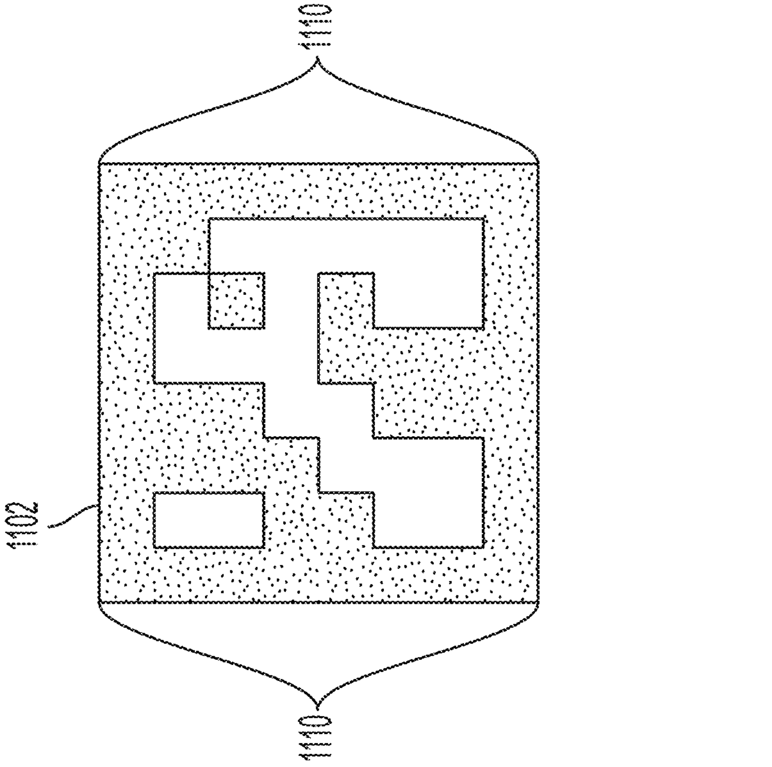

An example of the use of a fiducial marker to determine a position of a tip of a pointer tool, according to step 806, is illustrated in FIGS. 10, 11A, and 11B. FIG. 10 illustrates an exemplary coordinate system for a pointer of an exemplary pointer tool. The exemplary pointer 1000 of FIG. 10 includes a tip 1002 and two sets of fiducial markers 1004 and 1006. Each set of fiducial markers 1004 and 1006 includes a plurality of corners 1008. In the example shown in FIG. 10, a coordinate system has been superimposed on the pointer 1000 to illustrate how the positions of corners 1008 can be used to determine the position of the tip 1002 of the pointer 1000. The tip 1002 of the pointer 1000 can represent the origin (0, 0, 0) of the coordinate system, and the coordinates of each of the corners 1008 of the sets of fiducial markers 1004 and 1006 represent the distances along the x-axis, y-axis, and z-axis (the z-axis is out of the page) from the tip. These distances are predetermined and may be stored in a database that is accessible to an image processing system. The example of FIG. 10 illustrates that when a three-dimensional position of any of the corners 1008 is determined, the position of the tip 1002 can be determined using predetermined positional relationships between the corners 1008 and the tip 1002. Although the fiducial markers 1004 and 1006 are illustrated as being formed on flat surfaces, it should be understood that the same principles for determining the position of the tip of the pointer tool apply to examples having fiducial markers formed on one or more curved surfaces.

FIGS. 11A and 11B illustrate an exemplary ArUco marker that can be disposed on a pointer tool. In the example of FIGS. 11A and 11B, an ArUco marker 1102 can include a plurality of dark-colored (e.g., black) and light-colored (e.g., white) blocks 1106 in a specific arrangement that allows the ArUco marker 1102 to be uniquely identified. The blocks of the ArUco marker 1102 are arranged in a grid. FIG. 11B shows the ArUco marker 1102 with a grid superimposed on the ArUco marker 1102 to better illustrate the plurality of blocks. The ArUco marker 1102 can include, for example, 64 blocks that are arranged on an 8×8 matrix. The ArUco marker 1102 can include a border 1108 that frames the ArUco marker 1102. In one or more examples, the border 1108 can be disposed on the first row, the last row, the first column, and the last column of the ArUco marker 1102. In the example of an 8×8 matrix, the border 1108 can be arranged to leave an internal 11×6 matrix. Each block 1106 of the internal 6×6 matrix can either be a dark block or a light block. The examples of an 8×8 matrix and 6×6 internal matrix are meant as examples only and should not be seen as limiting to the disclosure. Thus, in one or more examples, a particular ArUco marker can be configured in a variety of dimensions and grid layouts without departing from the scope of the present disclosure.

In one or more examples, the light and dark blocks can be arranged on the 6×6 internal matrix to provide the ArUco marker 1102 with a unique arrangement that can be used to uniquely identify the ArUco marker 1102. An image processing system can determine the arrangement of the blocks 1106 of the ArUco marker 1102 and can obtain the positions of the corners 1110 of the ArUco marker 1102 (e.g., the corners of the 8×8 matrix). The image processing system can use the determined arrangement of the blocks 1106 to extract the identity of the ArUco marker 1102. The image processing system can then access a database that includes predetermined positions of the corners of ArUco markers relative to the tip of a pointer tool and extract the predetermined positions of the corners 1110 of the identified ArUco marker 1102 relative to the tip of the pointer tool. For example, the image processing system can access a database that includes an (x, y, z) entry corresponding to each corner of each ArUco marker and can obtain the (x, y, z) entries for the corners of a given ArUco marker based on the identity of the ArUco marker extracted from its unique arrangement of blocks. The image processing system can combine the positions of the corners 1110 of the ArUco marker 1102 with the predetermined positions of the corners 1110 of the identified ArUco marker 1102 relative to the tip of the pointer tool to determine the position of the tip of the pointer tool.

The position of the surgical tool or portion thereof determined in step 806 can be used in any number of ways. For example, the determined position of the tip 228 of pointer tool 200 could be used to provide a graphical indication of the location of the tissue of interest proximate the tip in one or more endoscopic images displayed to a user, to track a particular location of the tissue of interest over an imaging session or portion of an imaging session, and/or to generate one or more measurements associated with the location of the tip relative to the tissue of interest.

Optionally, one or more machine learning models can be used in combination with one or more steps of process 800 of FIG. 8. For example, one or more machine learning models can detect a pointer tool or other surgical tool in an endoscopic image received at step 802 and the detection of the pointer tool can be used to trigger and/or facilitate the detection of fiducial markers in step 804. A machine learning model can be trained using a supervised training process in which images or videos of the pointer tool are annotated with the precise location of the tool in the image, so that the machine learning model (for instance, a convolutional neural network (CNN)) can recognize the presence and location of a pointer tool in a given image. A machine learning model can be trained to analyze endoscopic video to detect the presence of a pointer tool in the video, determine a location of the pointer tool in the video, and track the pointer tool in the video over time. Such a machine learning model can be a convolutional long short-term memory (convolutional LSTM) model that utilizes both spatial and temporal features of endoscopic video and is trained in a weakly supervised regime (e.g., where each label indicates a presence or absence of one or more pointer tools, without providing their locations).

In some examples, an image processing system, such as image processing unit 116 of system 100, uses a machine learning model to detect a particular use of a pointer tool that is indicative of a need to determine a position of a tip of the pointer tool and, in response to such a detection, to automatically initiate one or more steps of process 800 of FIG. 8. The machine learning model can be a deep learning model trained to simultaneously perform pointer tool tracking, rough localization of the tip of the pointer tool, and recognition of an action performed using the pointer tool. The deep learning model can be an "instrument-verb-target" model trained to process video to detect an instrument (e.g., a pointer tool), performing an action (e.g., pointing), with respect to a target (e.g., bony tissue of a joint). For example, the "instrument-verb-target" model may detect, in video, a pointer tool moving toward bony tissue of a joint and then stopping (e.g., for some period of time indicative of a pointing action by a user) and may determine that this activity of the pointer tool is indicative that the pointer tool is pointing to the bony tissue.

In some examples, an "instrument-verb-target" machine learning model can continuously process incoming video to detect use of the pointer tool to point to tissue. For example, referring to process 800 of FIG. 8, images received at step 802 can be processed by an "instrument-verb-target" machine learning model to detect use of a pointer tool to point to tissue. The detection of such an action can then trigger performance of step 804, which is described in detail above.

In some examples, the "instrument-verb-target" machine learning model can identify a region of the image containing the tip region of the pointer tool and the fiducial marker(s) and this information can be used in step 804 to reduce the amount of image data that is processed to locate the fiducial marker(s) in step 804, which can make locating the fiducial marker faster than processing an entire image. In other words, instead of step 804 including the processing of an entire image to locate the fiducial marker(s), processing may be limited to the region(s) of the image identified by the "instrument-verb-target" machine learning model. Optionally, one or more image enhancement techniques may be applied to the region(s) of the image identified by the "instrument-verb-target" machine learning model to improve the identification of the fiducial marker(s) in step 804, which may also reduce the amount of processing relative to a process that applies image enhancement techniques to the entire image.

Although the above refers to the "instrument-verb-target" machine learning model detecting the use of a pointer tool, this is merely exemplary, and it should be understood that the "instrument-verb-target" machine learning model can be trained to detect the use of any tool, including, for example, a cutter, drill, or any other surgical tool. Additionally, the detection of a suitable action need not lead to (or only to) step 804. In some examples, a notification associated with the detection of the action can be provided to the user. For example, the detection of the use of a pointer tool can lead to a display, on a graphical user interface of a function guide that guides the user in using the pointer tool, for example, to define a measurement point. In some examples in which the tool detected is a cutter or drill and the target is tissue that should be avoided, an alert may be provided to the user alerting the user that the cutter or drill is too close to the tissue. An example of a suitable "instrument-verb-target" machine learning model is described in Nwoye et al., "Rendezvous: Attention Mechanisms for the Recognition of Surgical Action Triplets in Endoscopic Videos," arXiv: 2019.03223v2 (Mar. 3, 2022), which is incorporated by reference in its entirety. The machine learning model can be trained with video data in which frames of the video data are labeled with suitable "instrument-verb-target" labels. For example, frames of respective training videos that include a pointer tool that is being used to point to a bony structure of a joint can be labeled with "pointer tool-pointing-bony structure." The machine learning model can then be trained with such training videos to detect the use of a pointer tool to point to the bony structure.

Figure 9:
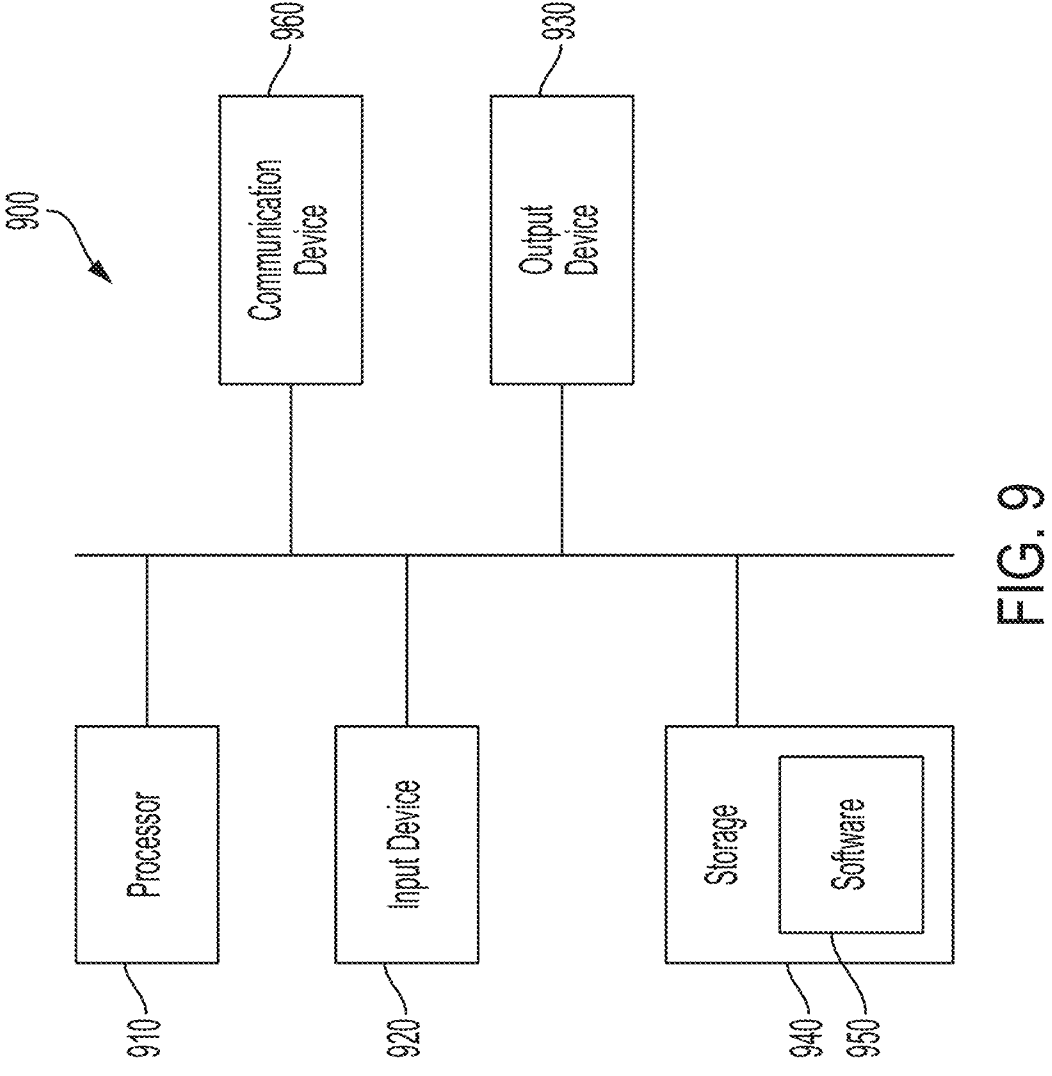
FIG. 9 is a block diagram of an exemplary computing system.

FIG. 9 illustrates an example of a computing system 900, in accordance with some embodiments, that can be used for one or more components of system 100 of FIG. 1, such as one or more of camera head 108, camera control unit 112, image processing unit 116, and tool controller 126. System 900 can be a computer connected to a network, such as one or more networks of hospital, including a local area network within a room of a medical facility and a network linking different portions of the medical facility. System 900 can be a client or a server. As shown in FIG. 9, system 900 can be any suitable type of processor-based system, such as a personal computer, workstation, server, handheld computing device (portable electronic device) such as a phone or tablet, or dedicated device. The system 900 can include, for example, one or more of input device 920, output device 930, one or more processors 910, storage 940, and communication device 960. Input device 920 and output device 930 can generally correspond to those described above and can either be connectable or integrated with the computer.

Input device 920 can be any suitable device that provides input, such as a touch screen, keyboard or keypad, mouse, gesture recognition component of a virtual/augmented reality system, or voice-recognition device. Output device 930 can be or include any suitable device that provides output, such as a display, touch screen, haptics device, virtual/augmented reality display, or speaker.

Storage 940 can be any suitable device that provides storage, such as an electrical, magnetic, or optical memory including a RAM, cache, hard drive, removable storage disk, or other non-transitory computer-readable medium. Communication device 960 can include any suitable device capable of transmitting and receiving signals over a network, such as a network interface chip or device. The components of the computing system 900 can be connected in any suitable manner, such as via a physical bus or wirelessly.

Processor(s) 910 can be any suitable processor or combination of processors, including any of, or any combination of, a central processing unit (CPU), field programmable gate array (FPGA), graphics processing unit (GPU), and application-specific integrated circuit (ASIC). Software 950, which can be stored in storage 940 and executed by one or more processors 910, can include, for example, the programming that embodies the functionality or portions of the functionality of the present disclosure (e.g., as embodied in the devices as described above), such as programming for performing one or more steps of method 800.

Software 950 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 940, that can contain or store programming for use by or in connection with an instruction execution system, apparatus, or device.

Software 950 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport computer-readable medium can include, but is not limited to, an electronic, magnetic, optical, electromagnetic, or infrared wired or wireless propagation medium.

System 900 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 900 can implement any operating system suitable for operating on the network. Software 950 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for the purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application is hereby incorporated herein by reference.

The invention claimed is:

1. A surgical tool for an endoscopic procedure comprising:

a proximal portion comprising a shaft; and a black polymer distal portion mounted to a distal end of the shaft such that the black polymer distal portion extends distally of the shaft, the black polymer distal portion configured for at least partial insertion in a surgical cavity of a patient during the endoscopic procedure, the black polymer distal portion comprising a plurality of planar surfaces comprising a plurality of laser-marked fiducial markers for detection by an endoscopic imaging system, wherein the black polymer distal portion comprises a first portion extending along a longitudinal axis and a second portion that extends transversely to the longitudinal axis, wherein the first portion comprises a first planar surface of the plurality of planar surfaces and the second portion comprises a second planar surface of the plurality of planar surfaces, the first and second portions having fixed positions with respect to each other and being positioned and oriented such that the first and second planar surfaces are capable of being shown in a common endoscopic image.

2. The surgical tool of claim 1, wherein the plurality of laser-marked fiducial markers comprise lighter regions and darker regions, the lighter regions having been laser marked, the darker regions not having been laser marked.

3. The surgical tool of claim 2, wherein a width of at least one darker region is the same as a width of at least one lighter region.

4. The surgical tool of claim 1, wherein the black polymer distal portion comprises: (a) Delrin, Radel, Acrylonitrile Butadiene Styrene (ABS), an acetal copolymer, or nylon; and (b) a carbon colorant.

5. The surgical tool of claim 1, wherein the plurality of laser-marked fiducial markers were laser marked with a laser having a wavelength less than or equal to 2,100 nm.

6. A method of endoscopic imaging comprising, at a computing system:

receiving at least one endoscopic image that captures a surgical tool positioned in a surgical cavity, the surgical tool comprising a shaft, and a black polymer distal portion mounted to a distal end of the shaft such that the black polymer distal portion extends distally of the shaft, the black polymer distal portion comprising a plurality of planar surfaces comprising a plurality of laser-marked fiducial markers, wherein the black polymer distal portion comprises a first portion extending along a longitudinal axis and a second portion that extends transversely to the longitudinal axis, wherein the first portion comprises a first planar surface of the plurality of planar surfaces and the second portion comprises a second planar surface of the plurality of planar surfaces, the first and second portions having fixed positions with respect to each other and being positioned and oriented such that the first and second planar surfaces are capable of being shown in a common endoscopic image;

detecting in the at least one endoscopic image at least one laser-marked fiducial marker of the plurality of laser-marked fiducial markers; and determining a position of at least a portion of the surgical tool in the surgical cavity based on the at least one laser-marked fiducial marker.

7. The method of claim 6, wherein the at least one laser-marked fiducial marker comprises a laser marked perimeter and determining the position of the at least a portion of the surgical tool comprises determining a location of at least one corner of the laser marked perimeter.

8. The method of claim 6, wherein the at least one laser-marked fiducial marker comprises lighter regions and darker regions, the lighter regions having been laser marked, the darker regions not having been laser marked, and wherein a width of at least one darker region is the same as a width of at least one lighter region.

9. The method of claim 6, wherein a size of the at least one laser-marked fiducial marker is less than 3 mm×3 mm.

10. The method of claim 6, wherein the at least one laser-marked fiducial marker is an ArUco marker.

11. The method of claim 6, wherein the plurality of laser-marked fiducial markers comprises a first fiducial marker that is oriented transversely relative to a second fiducial marker.

12. The method of claim 6, wherein the black polymer distal portion comprises Delrin, Radel, Acrylonitrile Butadiene Styrene (ABS), an acetal copolymer, or nylon.

13. The method of claim 6, wherein the black polymer distal portion comprises a carbon colorant.

14. The method of claim 6, wherein the surgical tool is a pointer tool.

15. The method of claim 6, wherein the at least one laser-marked fiducial marker was laser marked with a laser having a wavelength less than or equal to 2,100 nm.

16. A system comprising one or more processors, memory, and one or more programs stored in the memory for execution by the one or more processors to cause the system to:

receive at least one endoscopic image that captures a surgical tool positioned in a surgical cavity, the surgical tool comprising a shaft, and a black polymer distal portion mounted to a distal end of the shaft such that the black polymer distal portion extends distally of the shaft, the black polymer distal portion comprising a plurality of planar surfaces comprising a plurality of laser-marked fiducial markers, wherein the black polymer distal portion comprises a first portion extending along a longitudinal axis and a second portion that extends transversely to the longitudinal axis, wherein the first portion comprises a first planar surface of the plurality of planar surfaces and the second portion comprises a second planar surface of the plurality of planar surfaces, the first and second portions having fixed positions with respect to each other and being positioned and oriented such that the first and second planar surfaces are capable of being shown in a common endoscopic image;

detect in the at least one endoscopic image at least one laser-marked fiducial marker of the plurality of laser-marked fiducial markers; and determine a position of at least a portion of the surgical tool in the surgical cavity based on the at least one laser-marked fiducial marker.

17. The system of claim 16, wherein the at least one laser-marked fiducial marker was laser marked with a laser having a wavelength less than or equal to 2,100 nm.

18. The surgical tool of claim 1, wherein the black polymer distal portion comprises black Delrin.

19. The surgical tool of claim 1, wherein the plurality of laser-marked fiducial markers were marked via a laser scan speed of 800-1,200 mm/s.

20. The surgical tool of claim 1, wherein the plurality of laser-marked fiducial markers were marked via a laser pulse frequency of 35-45 kHz.

21. The surgical tool of claim 1, wherein the shaft is made from a different material than the black polymer distal portion.

* * * * *